US011432712B2

(12) United States Patent
Duckett, III et al.

(10) Patent No.: US 11,432,712 B2
(45) Date of Patent: Sep. 6, 2022

(54) FLUORESCENCE IMAGING SCOPE WITH DUAL MODE FOCUSING STRUCTURES

(71) Applicant: KARL STORZ Imaging, Inc., Goleta, CA (US)

(72) Inventors: George E. Duckett, III, Castaic, CA (US); Russell Granneman, Goleta, CA (US); Daniel Lietz, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 829 days.

(21) Appl. No.: 15/636,345

(22) Filed: Jun. 28, 2017

(65) Prior Publication Data

US 2019/0000308 A1 Jan. 3, 2019

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/0019* (2013.01); *A61B 1/00105* (2013.01);
(Continued)

(58) Field of Classification Search
None
See application file for complete search history.

(56) References Cited

U.S. PATENT DOCUMENTS 8,330,087 B2 12/2012 Domenicali
8,773,756 B2 7/2014 Tesar
(Continued)

FOREIGN PATENT DOCUMENTS

JP 2013180120 A * 9/2013
JP 2013180120 A 9/2013
WO 2011113062 A1 9/2011

OTHER PUBLICATIONS

Alvazzi Delfrate, S., Extended European Search Report for European Application No. EP 18000533, dated Nov. 14, 2018, pp. 1-16, Munich, Germany.
(Continued)

*Primary Examiner* — Kaitlin A Retallick
(74) *Attorney, Agent, or Firm* — Michael J. Loi; David Noel Villapando (57) ABSTRACT

Improved fluoresced imaging (FI) and other sensor data imaging processes, devices, and systems are provided to enhance use of endoscopes with FI and visible light capabilities. A first optical device is provided for endoscopy imaging in a white light and a fluoresced light mode with an image sensor assembly including one or more image sensors. A mechanism in the first optical device to automatically adjust the focus of the first optical device wherein the automatic focus adjustment compensates for a chromatic focal difference between the white light image and the fluoresced light image caused by the dispersive or diffractive properties of the optical materials or optical design employed in the construction of the first or second optical devices, or both. Adjustment mechanisms are provided using liquid lenses or repositioning sensors. The design may be integrated with a scope or detachable.

10 Claims, 6 Drawing Sheets

(51) Int. Cl.
  *A61B 1/06* (2006.01)
  *A61B 1/05* (2006.01)
  *G02B 3/14* (2006.01)
  *G02B 23/24* (2006.01)
  *H04N 5/225* (2006.01)
  *H04N 5/33* (2006.01)

(52) U.S. Cl.
  CPC ...... *A61B 1/00133* (2013.01); *A61B 1/00188* (2013.01); *A61B 1/042* (2013.01); *A61B 1/053* (2013.01); *A61B 1/0638* (2013.01); *G02B 3/14* (2013.01); *G02B 23/2446* (2013.01); *G02B 23/2484* (2013.01); *H04N 5/2256* (2013.01); *H04N 5/332* (2013.01); *H04N 2005/2255* (2013.01)

(56) References Cited

U.S. PATENT DOCUMENTS

| | | | |
|---|---|---|---|
| 2005/0219688 A1 | 10/2005 | Kawano et al. | |
| 2005/0283058 A1 | 12/2005 | Choo-Smith et al. | |
| 2006/0012836 A1* | 1/2006 | Boemler | H04N 5/23212 348/E5.045 |
| 2007/0030345 A1* | 2/2007 | Amling | A61B 1/045 348/73 |
| 2008/0303899 A1* | 12/2008 | Berci | A61B 1/055 600/112 |
| 2009/0236541 A1* | 9/2009 | Lomnes | A61B 1/05 250/458.1 |
| 2010/0245550 A1* | 9/2010 | Ishihara | A61B 1/00186 348/68 |
| 2012/0002956 A1 | 1/2012 | McDowall | |
| 2012/0194728 A1* | 8/2012 | Kim | G02B 3/00 348/E5.024 |
| 2013/0038689 A1* | 2/2013 | McDowall | H04N 5/2355 348/45 |
| 2014/0272767 A1 | 9/2014 | Monty | |
| 2017/0205341 A1* | 7/2017 | Gillet | G01J 3/0208 |

OTHER PUBLICATIONS

Dole, A., Communication pursuant to Article 94(3) EPC for European Application No. EP 18000533, dated Jan. 27, 2022, pp. 1-4, Munich, Germany.

* cited by examiner

FLUORESCENCE IMAGING SCOPE WITH DUAL MODE FOCUSING STRUCTURES

TECHNICAL FIELD OF THE INVENTION

The invention relates generally to the field of image capture and more specifically to a medical imaging camera head and camera designs for attaching or integrating with endoscopes capable of fluorescent imaging and visible color imaging.

BACKGROUND OF THE INVENTION

Endoscopes and other medical scopes often use fluorescing agents or autofluorescence to better examine tissue. A fluorescing agent such as a dye may be injected or otherwise administered to tissue, and then an excitation light is directed toward the tissue. Responsive to the excitation light, the fluorescing agent fluoresces (emits light typically at a longer wavelength than the excitation light), allowing a sensor to detect the light, which is often not in a wavelength visible to the human eye. The detected light is formatted to images, and examining the images can indicate the concentration of fluorescing agent in the observed tissue. Further, a phenomenon known as autofluorescence may occur in which tissue fluoresces light under certain conditions without a fluorescing agent. Such light can be detected as well. Images based on detected fluoresced light, known as "fluorescence imaging" (FI), are therefore useful in medical diagnosis, testing, and many scientific fields.

Figure 1:
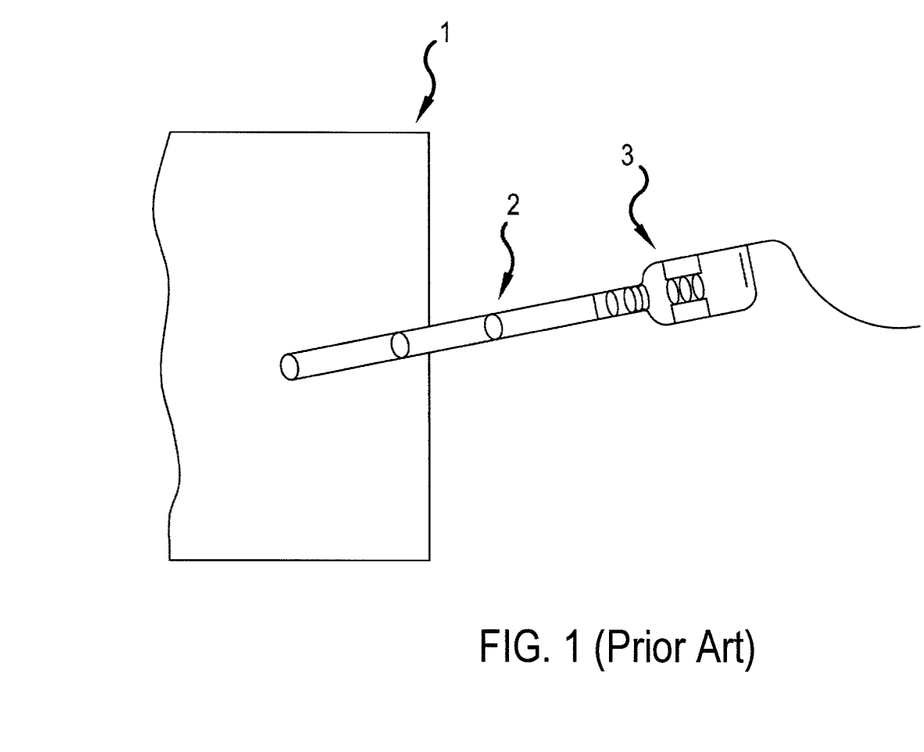
FIG. 1 is diagram of a prior art endoscopic system.

A typical prior art endoscope 2, as illustrated in FIG. 1, usually includes a first imaging lens (e.g., an objective) followed by a series of carrier lenses (e.g., relays) which capture and transmit an optical image from inside an enclosed area 1 to the outside. The proximal end of the endoscope 2 may be attached, via direct coupling or an adaptor, to a camera head 3 or an eye-piece for viewing. The camera head 3 usually includes lenses for receiving the optical image and forming a real optical image onto the image sensor. The digital image captured by the image sensor can then be transmitted to a camera control unit (CCU) or other similar modules for analysis and display.

Frequently, endoscopes used for FI applications, and particularly indocyine green (ICG) applications are mainly designed and deployed for visible light imagery. To perform FI imaging, such scopes often employ an appropriate optical filter to block the stimulus light and transmit the fluoresced light. Since these endoscopes are designed for use with visible light (approximately 450-650 nm wavelengths), the infrared fluorescence (800-900 nm) is focused in a different plane than the visible light. Therefore, in addition to adding a filter, the user must refocus when switching between visible light mode and fluorescence mode unless the camera compensates. The focal differences exist because the endoscopes are not chromatically corrected for the infrared where certain fluorescence bands (particularly ICG) are located. Such differences, even in the face of common correction techniques, often result in a signal to noise ratio of FI imaging being low, resulting in poor quality FI images. Given the dispersion characteristics of optical elements used in the endoscope's optical channel, such as rod lenses, correcting these issues may be difficult or expensive. For example, when autofocus algorithms are employed, the algorithm is frequently slow to apply the correction.

What is needed are devices and methods to enable an endoscopic camera to compensate for the endoscope characteristics when the user switches between white light mode and fluorescence mode. What is further needed are devices allowing the use of varied existing endoscopes for fluorescence imaging applications without expensive and slow optical elements such as autofocus mechanisms or lenses and processing systems for chromatic aberration correction.

SUMMARY OF THE INVENTION

It is an object of the invention to provide improved endoscopic camera devices and methods to enable the camera to compensate for the endoscope characteristics when the user switches between white light mode and fluorescence mode. Another object of the invention is to enable such switching in an automated manner without the user inserting filters or manually refocusing a device to achieve a switch between FI to visible light modes. Another object of the invention is to enable the use of existing endoscopes in simultaneous FI and visible light modes. Is it a further object of the invention to provide devices and methods allowing the use of varied existing endoscopes for fluorescence imaging applications without expensive optical elements such as autofocus mechanisms or lenses and processing systems for chromatic aberration correction.

In order to achieve these objects, various aspects of the invention provide improved fluoresced imaging (FI) and other sensor data imaging processes, devices, and systems are provided to enhance use of endoscopes with FI and visible light capabilities. A first optical device is provided for endoscopy imaging in a white light and a fluoresced light mode with an image sensor assembly including one or more image sensors. A focus adjustment mechanism in the first optical device to automatically adjust the focus of the first optical device wherein the automatic focus adjustment compensates for a chromatic focal difference between the white light image and the fluoresced light image caused by the dispersive or diffractive properties of the optical materials or optical design employed in an assembly construction of the first or second optical devices, or both. Adjustment mechanisms are provided using liquid lenses or repositioning sensors. The design may be integrated with a scope or detachable.

According to a first aspect of the invention, a first optical device is provided for use in endoscope procedures and operable to image in a first mode with white light and a second mode with fluoresced light outside the visible band. The first optical device includes an image sensor assembly including one or more image sensors operable for capturing white light images and fluoresced light images. A focus adjustment mechanism is positioned in the first optical device to automatically adjust the focus of the first optical device wherein the automatic focus adjustment compensates for a chromatic focal difference between the white light image and the fluoresced light image caused by the dispersive or diffractive properties of the optical materials or optical design employed in an assembly construction of the first optical device or an optional second optical device connected to the first optical device, or both.

According to a second aspect of the invention, a first optical device is provided for use in endoscope procedures and operable to image in a first mode with white light and a second mode with fluoresced light outside the visible band. The first optical device includes an image sensor assembly including one or more image sensors operable for capturing white light images and fluoresced light images. An optical assembly is positioned in the first optical device, or in the second optical device, the optical assembly including one or more optical lens elements, all either fixed in place or adjustable by manual movements, and is configured when attached to direct light received from a subject scene toward the image sensor assembly. A liquid-based deformable lens is provided in the first optical device optically arranged to be between the optical assembly and the image sensor and operable to automatically adjust the focus of the first optical device wherein the automatic focus adjustment compensates for a chromatic focal difference between the white light image and the fluoresced light image caused by the dispersive or diffractive properties of the optical materials or optical design employed in an assembly construction of the first optical device or the second optical device, or both.

According to a third aspect of the invention, a first optical device is provided for use in endoscope procedures and operable to image in a first mode with white light and a second mode with fluoresced light outside the visible band. The first optical device includes an image sensor assembly including one or more image sensors operable for capturing white light images and fluoresced light images. An optical assembly is positioned in the first optical device, or in a second optical device that attaches to the first optical device, the optical assembly including one or more optical lens elements, all either fixed in place or adjustable by manual movements, and is configured when attached to direct light received from a subject scene toward the image sensor assembly. The first optical device includes a mechanical device which shifts the position of at least one of the one or more image sensors when the mode is switched from white light mode to fluoresced light mode and operable to automatically adjust the focus of the first optical device wherein the automatic focus adjustment compensates for a chromatic focal difference between the white light image and the fluoresced light image caused by the dispersive or diffractive properties of the optical materials or optical design employed in an assembly construction of the first optical device or the second optical device, or both.

In some implementations of the various aspects of the invention, the first optical device is a videoendoscope. In some other implementations, the first optical device is camera head that attaches to and detaches from the second optical device, and the second optical device is an endoscope. The camera head may configured to automatically recognize the second optical device and, in response, automatically apply a known, prescribed adjustment based on known characteristics of the second optical device.

In some implementations of the various aspects of the invention, the adjustment made is a known, prescribed adjustment based on the known characteristics of the first optical device and/or the second optical device. The focus adjustment mechanism may include a liquid-based deformable lens. The device may be adapted to toggle the liquid-based deformable lens between two pre-determined states when the mode is switched from white light mode to fluoresced light mode. The sensor position may toggle between two pre-determined positions when the mode is switched from white light mode to fluoresced light mode. In some implementations of the various aspects of the invention, the focus adjustment includes a mechanical device which shifts the position of at least one of the one or more image sensors when the mode is switched from white light mode to fluoresced light mode. The mechanical device may be a motor, such as a piezoelectric motor.

In some implementations of the various aspects of the invention, the device is adapted to trigger the automatic focus adjustment when the device is toggled between white light mode and fluorescence mode. The first device may include an electronic controller having tangible, non-transitory computer memory holding program code executable to control the various adjustments, and to trigger the automatic focus adjustment when the device is toggled.

Implementations of the invention may also be embodied according to a fourth aspect of the invention as software or firmware, stored in a suitable medium, and executable to perform various versions of the methods herein. The program code is executable to control the various adjustments, and to trigger the automatic focus adjustment when the device is toggled. According to a fifth aspect, the functionality described herein for the implementations of the first aspect may be embodied as a method or process for operating an imaging scope to perform the automatic focus adjustment. The method may include automatically recognizing the connection of an endoscope device to a camera head embodying the first optical device. The method may retrieve focus settings for the different modes from memory, and may store focus settings for multiple devices. The method applies the retrieved focus settings and allows procedures to be conducted in the white light imaging mode. In response to a user changing to a fluorescence imaging mode, the method applies retrieved focus settings for the fluorescence imaging mode according to any of the different device aspects of the invention. Then the method allows procedures in the fluorescence imaging mode, and allows the modes to be toggled as needed with the appropriate focus settings applied for each toggle.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras and FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 2:
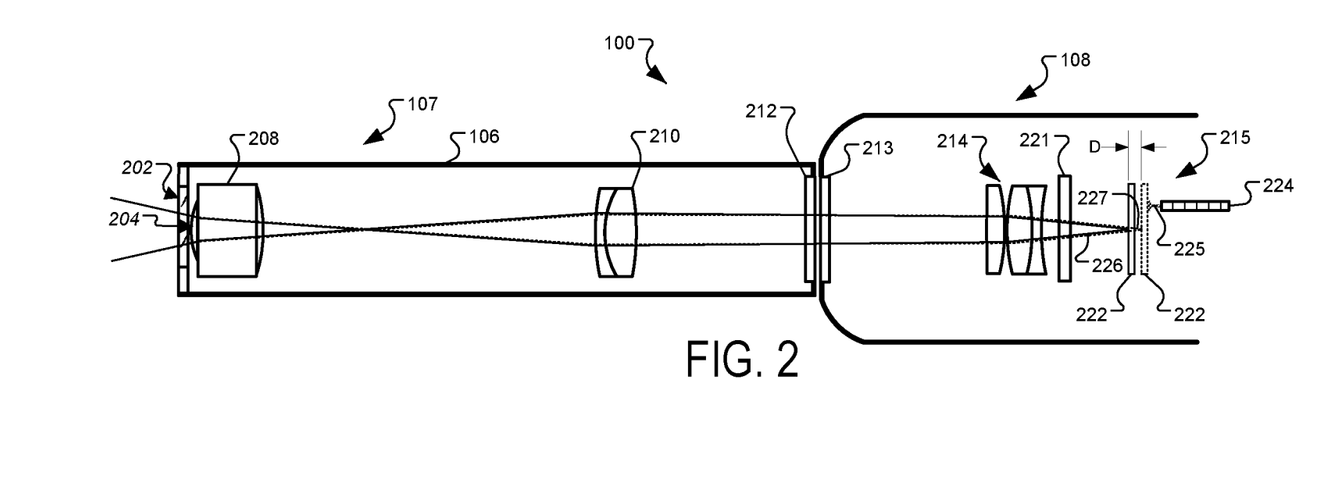
FIG. 2 shows cross section diagram of a video endoscope device according to an example embodiment of the invention.

FIG. 2 shows cross section diagram of a video endoscope device 100 according to an example embodiment of the invention. This device 100 includes a first optical device 108 (in this version "camera head 108") connected in a detachable manner to endoscope 107 ("second optical device") which is connected to in a detachable manner as known in the art. Endoscope 107 includes a shaft 106. Other versions may, of course, include a scope integrated with the camera head or in a single first optical device. Various structural components supporting the depicted elements are omitted in the diagram, as well as other components such as illumination lights sources, fluorescent excitation light sources, and controls, which are known in the art and are not shown in order to avoid obscuring the relevant details of the example embodiments of the invention.

Toward the left side of the drawing, at the distal tip of the endoscope shaft 106 is cover glass 202, which in this version faces directly along the longitudinal axis of the shaft 106, but may also be positioned at an angle relative to the longitudinal axis as is known in the art. Behind the cover glass 202 is shown a preferred position for the wide angle lens 204, set against or very near cover glass 202 and preferably assembled together with the cover glass in construction. While a wide angle lens is shown, this is not limiting and any suitable lens may be used in various embodiments. Further, the particular number and arrangement of lenses in the endoscope shaft 106 will vary widely depending on the application. Optically arranged or attached at the proximal side of lens 204 is a second lens or lens group 208 to focus the incoming light to an appropriate size for the imaging process receiving the incoming light downstream in the proximal direction. The directed light then passes along endoscope shaft 106, and may be guided by other optical elements such as rod lenses. Next the light is received at a doublet lens 210, and directed toward first optical device 108, where it passes through the proximal window 212 of the endoscope 107 and the distal window 213 of first optical device 108. One or more additional lens groups or rod lenses may be included optically positioned between doublet lens 210 and focusing lens group 214. In versions with a unified device, such windows may not be used. Next in the optical path is a focusing lens group 214 which in this version includes a plano-convex lens and a doublet lens including a biconvex lens and a biconcave lens. Many other suitable lenses and combinations of lenses may be used. Focusing lens group 214 focuses the image light toward the image sensor assembly 215 which may include a cover glass 221 and image sensor 222.

As shown, image sensor 222 is repositionable along the focal path by an adjustment mechanism 224, which may be a piezo-electric motor or other suitable adjustment mechanism. Adjustment mechanism 224 is shown mechanically coupled to sensor 222 with a rod 225, which pushes or pulls image sensor 222 to achieve the adjustment movement. Image sensor 222 may be held in a frame having guide rails or other suitable structure to stabilize the orientation during movement. In this version, image sensor 222 is a single sensor capable of detecting both visible light images and fluoresced light images, for example visible light imagery at approximately the 450-650 nm wavelengths, and the infrared fluorescence imagery at 800-900 nm. Additionally or alternatively the sensor may detect other fluorescent wavelengths commonly used in endoscopic imagery in addition to the visible light wavelengths. Because the fluorescent imagery is focused in a different plane than the visible light, the device has the capability of adjusting the optical path focus when switching between visible light mode, as shown in the image sensor 222 first white light image position depicted as a solid box, and the second fluorescence mode image position depicted by the dotted box. The chromatic focal difference in the optical path are depicted by the two ray trace lines shown on the diagram, with the visible light ray trace 226 shown focused on the sensor 222 in the first depicted position in visible light mode, and the FI light ray trace 227 shown focused on sensor 222 in the FI mode position. The slight chromatic focal difference can be seen as the rays diverge slightly over the course of the optical path. The distance that image sensor 222 is moved, shown as D, is for adjusting the focal length of the optical path between white light imaging mode and fluorescent imaging mode. Typically this distance may be around 2 mm of movement, but this will vary depending on the total channel length and the chromatic characteristics of the optical elements in the optical channel. The adjustment mechanism 224 is positioned in the first optical device 108 to automatically adjust the focus of the first optical device where the automatic focus adjustment compensates for a chromatic focal difference between the white light image and the fluoresced light image caused by the dispersive or diffractive properties of the optical materials or optical design employed in the assembly construction of the first or second optical devices, or both. This may be accomplished even for endoscope designs in which the optical assembly includes optical lenses all either fixed in place or adjustable by manual movements. Preferably the act of a user changing modes to toggle between white light mode and fluorescence mode triggers an autofocus algorithm controlling the movement of adjustment mechanism 224. Preset positions may be employed for both modes to achieve the desired position, as further described below, avoiding the need for autofocus processing to achieve the known desired focal length for each of the modes.

Figure 3:
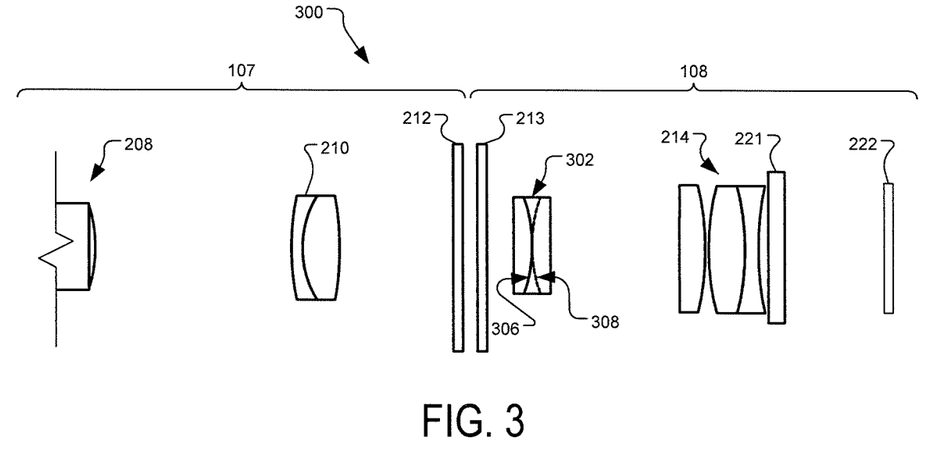
FIG. 3 is a cross section diagram of an optical channel having a deformable lens according to another embodiment for use in a video endoscopic system.

FIG. 3 is a cross section diagram of an optical channel 300 for use in a video endoscopic system according to another embodiment, which employs a deformable lens to adjust the focus. The depicted optical channel 300 may be embodied in first and second optical devices 107 and 108, such as the camera head and endoscope discussed above, or a single integrated optical device. The assembly construction of the second optical device, or the endoscope and shaft portion of an integrated device, may vary. As shown, the optical channel includes an objective passing the observed image light to one or more lens groups 208. The light is directed along the channel through a suitable lens arrangement such as doublet lens 210, and in detachable dual-device embodiments passes through windows 212 and 213 to the first optical device 108. Next in the optical path is the deformable lens 302, which is deformable to adjust the optical channel focal length for the same purpose of changing modes between white light imaging fluorescence imaging as discussed with regard to the other embodiments. The deformable lens can be made of, for example, birefringent liquid crystal, a transparent elastic membrane filled with fluid, or a two fluid interface. Preferably such a liquid-based deformable lens is employed, but other suitable deformable lens technologies may be used. Depicted are two different deformable surface configurations for the deformable lens. In the first white light imaging mode, deformable lens 302 is configured with the deformable surface at position 306, which generally has more negative lens power than the second fluoresced light configuration position of the deformable lens surface shown at dotted line 308. The deformable lenses can be tuned at least in part by a suitable adjustment mechanism (not shown) such as an electrostatic actuator, an electromagnetic actuator, a piezo-motor, a magneto-strictive actuator, a stepper motor, or an electroactive polymer actuator for a high focus tuning range. As depicted, the white light configuration position 306 is a negative power lens and the fluoresced light confirmation position 308 is a positive power lens, however this is not limiting, and they may both be negative or both may be positive depending on the optical channel design. Typically because the chromatic focal difference between the white light image and the fluoresced light image causes a shorter focal distance for the white light, the white light mode will have a comparatively negative lens power than the fluoresced light mode. The deformable lens 302 with its adjustment mechanism is arranged in the first optical device 108 to automatically adjust the focus of the first optical device where the automatic focus adjustment compensates for a chromatic focal difference between the white light image and the fluoresced light image caused by the dispersive or diffractive properties of the optical materials or optical design employed in the assembly construction of the first or second optical devices, or both. Preferably the act of a user changing modes to toggle between white light mode and fluorescence mode triggers an autofocus algorithm controlling the movement of adjustment mechanism 224. This design also may be accomplished even for endoscope designs in which the optical assembly includes optical lenses all either fixed in place or adjustable by manual movements. Preset positions may be employed for both modes to achieve the desired position, as further described below, avoiding the need for autofocus processing to achieve the known desired focal length for each of the modes.

Note that while the position of the deformable lens 302 is shown before the focusing lens group 214 in this version, this is not limiting and the deformable lens may be placed in any suitable location in the optical channel where the channel construction can accommodate the varied focal lengths resulting from changing the deformable lens configuration. For example, deformable lens 302 may be part of the focusing lens group 214.

After the deformable lens in the optical channel, the image light passes to the focusing lens assembly 214, which is similar to that described with respect to FIG. 2, and then through the image sensor cover glass 221 and finally to the image sensor 222. Note that in this version the image sensor is fixed in position relative to the optical channel.

Figure 4:
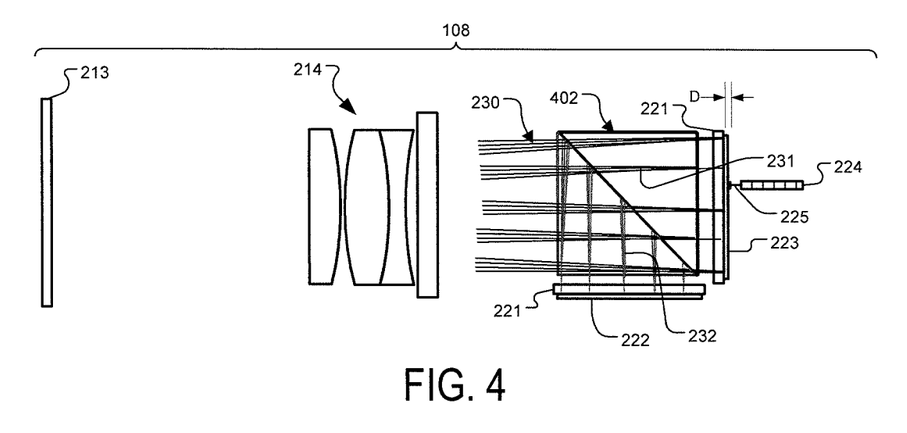
FIG. 4 is a cross section diagram of a partial optical channel having a light splitter and a focal adjustment after the optical channel is split according to another embodiment for use in a video endoscopic system.

FIG. 4 is a cross section diagram of a partial optical channel according to another embodiment. The diagram shows only the portion of the optical channel in first optical device 108, which is preferably a camera head device. In devices where the camera is combined with the endoscope, the diagram represents the proximal portion of the optical channel including the focusing lens group and the image sensor.

The depicted system uses a light splitter 402 to direct the visible image light to image sensor 222 and the fluoresced light to fluorescence image sensor 223. This is illustrated with the depicted light bundle traces 230 in which the fluorescence bundle traces 231 light enters and is passed through the dichroic prism interface of light splitter 402 and hits fluorescence image sensor 223, while the visible light bundle traces 232 are reflected downward and hit image sensor 222. Light splitter 402 is preferably a dichroic prism or other suitable dichroic optical element, having a high-pass reflective surface at a 45 degree angle allowing higher frequencies to pass through to fluorescence image sensor 223 and lower frequencies to reflect to sensor 222. The cutoff frequency may be positioned at or near the top wavelength of visible light, that is near 650 nm, or higher as long as it is below the lowest frequency (higher than longest wavelength) required for detection of the fluoresced light. While this version reflects the visible light wavelengths 232 and passes the fluoresced light wavelengths 231, this is not limiting and other versions may pass the visible light and reflect the fluoresced light (with a low-pass dichroic prism, for example), or may reflect both in differing directions.

Image sensor 222 is cable of detecting the visible light wavelengths commonly used for endoscopic examination, for example visible light imagery at approximately the 450-650 nm wavelengths. In this version, image sensor 223 is a single sensor capable of detecting fluoresced light images, infrared fluorescence imagery at 800-900 nm. Additionally or alternatively the sensor may detect other fluorescent wavelengths commonly used in endoscopic imagery.

As shown, fluorescence imaging sensor 223 is repositionable along the focal path by an adjustment mechanism 224 in order to adjust the focal plane for the fluoresced light based on characteristics of the attached endoscope, such as the aberration characteristics or the use of a differing fluoresced wavelengths in differing scopes for use with various fluoresced imaging techniques. This design also may be accomplished even for endoscope designs in which the optical assembly includes optical lenses all either fixed in place or adjustable by manual movements. The adjustment mechanism may be a piezo-electric motor or other suitable adjustment mechanism as discussed above with regard to the embodiment of FIG. 2. Similarly to the embodiment of FIG. 2, adjustment mechanism 224 is shown mechanically coupled to image sensor 223 with a rod 225, which pushes or pulls image sensor 223 to achieve the adjustment movement. Image sensor 223 may be held in a frame having guide rails or other suitable structure to stabilize the orientation during movement. The distance adjusted, shown as distance D, in this version will typically be less than that required to adjust for differing focal lengths between visible and fluoresced light, because this embodiments adjusts only for different fluoresced light characteristics of the optical channel such as dispersion and chromatic focal differences.

Figure 5:
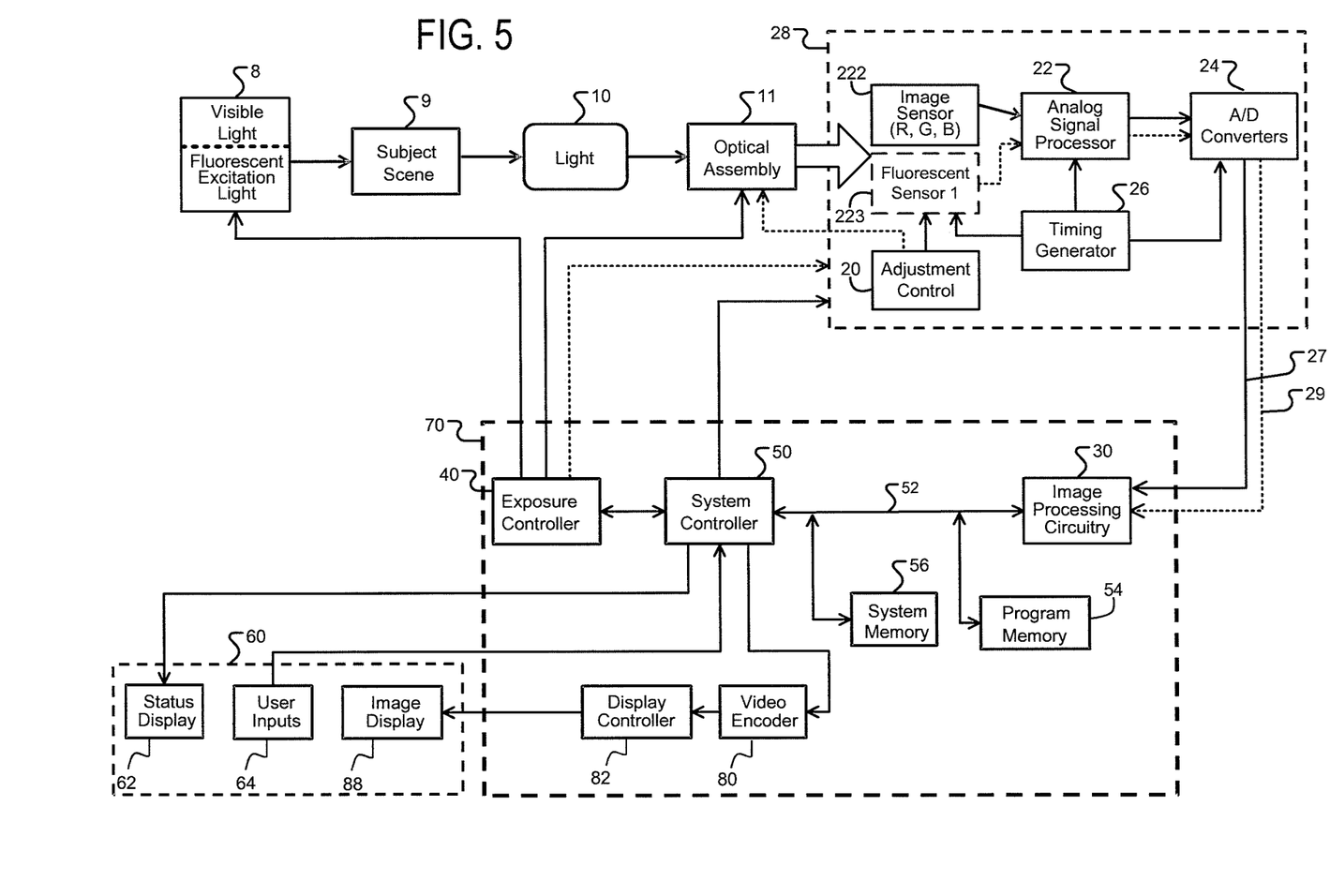
FIG. 5 is a hardware block diagram of system including an example image capture device according to an example embodiment of the invention.

Referring to FIG. 5, a block diagram of system including an image capture device according to an example embodiment of the invention is shown. The invention is applicable to more than one type of device enabled for image capture, such as endoscopes incorporating solid state imagers, digital microscopes, digital cameras, mobile phones equipped with imaging sub-systems, and automotive vehicles equipped with imaging sub-systems, for example. The preferred version is an imaging scope system, such as an endoscope.

A light source 8 illuminates subject scene 9 with visible light and/or fluorescent excitation light, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is focused to form an image at a solid-state image sensor(s) 222 and/or fluoresced light sensor(s) 223.

Optical assembly 11 includes at least one lens, which may be a wide-angle lens element such that optical assembly 11 focuses light which represents a wide field of view. In embodiments that employ a deformable lens as described above, the deformable lens 302 is part of the optical assembly. As discussed above, portions of the optical assembly may be embodied in a camera head or other first optical device, while other portions are in an endoscope or other scope device, or the optical assembly 11 may contained in a single imaging device. Image sensor 222 (which may include separate R, G, and B sensor arrays) and fluoresced light sensor 223 convert the incident visible and invisible light to an electrical signal by integrating charge for each picture element (pixel). It is noted that fluoresced light sensor 223 is shown as an optional dotted box because embodiments may use the RGB image sensor 222 to detect only white light images or to also detect fluoresced light (e.g., NIR, ICG, FI). The latter scheme may be used when the fluoresced light is in a spectrum detectable by image sensor 222 that is in or near the visible light spectrum typically detected by a RGB sensor arrays.

The image sensor 222 and fluoresced light sensor 223 may be active pixel complementary metal oxide semiconductor sensor (CMOS APS) or a charge-coupled device (CCD).

The total amount of light 10 reaching the image sensor 222 and/or fluoresced light sensor 223 is regulated by the light source 8 intensity, the optical assembly 11 aperture, and the time for which the image sensor 222 and fluoresced light sensor 223 integrates charge. An exposure controller 40 responds to the amount of light available in the scene given the intensity and spatial distribution of digitized signals corresponding to the intensity and spatial distribution of the light focused on image sensor 222 and fluoresced light sensor 223.

Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 222 and fluoresced light sensor 223 integrate charge. The control connection from exposure controller 40 to timing generator 26 is shown as a dotted line because the control is typically indirect.

Typically exposure controller 40 has a different timing and exposure scheme for each of sensors 222 and 223. Due to the different types of sensed data, the exposure controller 40 may control the integration time of the sensors 222 and 223 by integrating sensor 222 up to the maximum allowed within a fixed 60 Hz or 50 Hz frame rate (standard frame rates for USA versus European video, respectively), while the fluoresced light sensor 223 may be controlled to vary its integration time from a small fraction of sensor 222 frame time to many multiples of sensor 222 frame time. The frame rate of sensor 222 will typically govern the synchronization process such that images frames based on sensor 223 are repeated or interpolated to synchronize in time with the 50 or 60 fps rate of sensor 222.

Analog signals from the image sensor 222 and fluoresced light sensor 223 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 222 also functions to detect the fluoresced light, fluoresced light data is included in the image signal 27, typically in one or more of the three color channels.

An adjustment control circuit 20 may be provided for supplying the driving signals to operate the adjustment mechanism according to the various embodiments herein. For versions in which image sensor positions are adjusted, the adjustment control circuit sends appropriate driving signals to the mechanical adjustment mechanism, such as the piezo-electric motor, and may also receive position signals back from the adjustment mechanism. For versions in which a deformable lens 302 is employed, adjustment control circuitry 20 sends appropriate drive signals to the deformable lens adjustment mechanism, such as an actuator or piezo-electric motor, and may also receive position signals from the adjustment mechanism. Image processing circuitry 30 includes circuitry performing digital image processing functions to process and filter the received images as is known in the art. Image processing circuitry may include separate, parallel pipelines for processing the visible light image data and the FI image data separately. Such circuitry is known in the art and will not be further described here. In some embodiments, image processing circuitry 30 may also perform known autofocus algorithms to allow feedback control of adjustment control circuitry 20 to compensate for chromatic focal difference between the white light image and the fluoresced light image. However, in preferred embodiments, such adjustments are predetermined and stored in system memory 56 to allow quick and reliable focus adjustment. In some versions, the predetermined settings may be stored in memory in the first optical device itself rather than a CCM or other attached controller.

Image processing circuitry 30 may provide algorithms, known in the art, for combining visible light imagery with FI imagery in a combined image display, and further highlighting or emphasizing the FI imagery for easily distinguishing the presence of fluorescing features in the image.

Timing generator 26 produces various clocking signals to select rows and pixels and synchronizes the operation of image sensor 222 and fluorescent sensor 223, analog signal processor 22, and A/D converter 24. Image sensor assembly 28 includes the image sensor 222 and fluorescent sensor 223, adjustment control 20, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). System controller 50 may receive inputs from buttons or other external user interface controls on the scope itself (or software controls through the GUI) to receive inputs to control the process for automatically adjusting the focus according to the present invention. In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Such settings may include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control module (CCM) 70.

CCM 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 6:
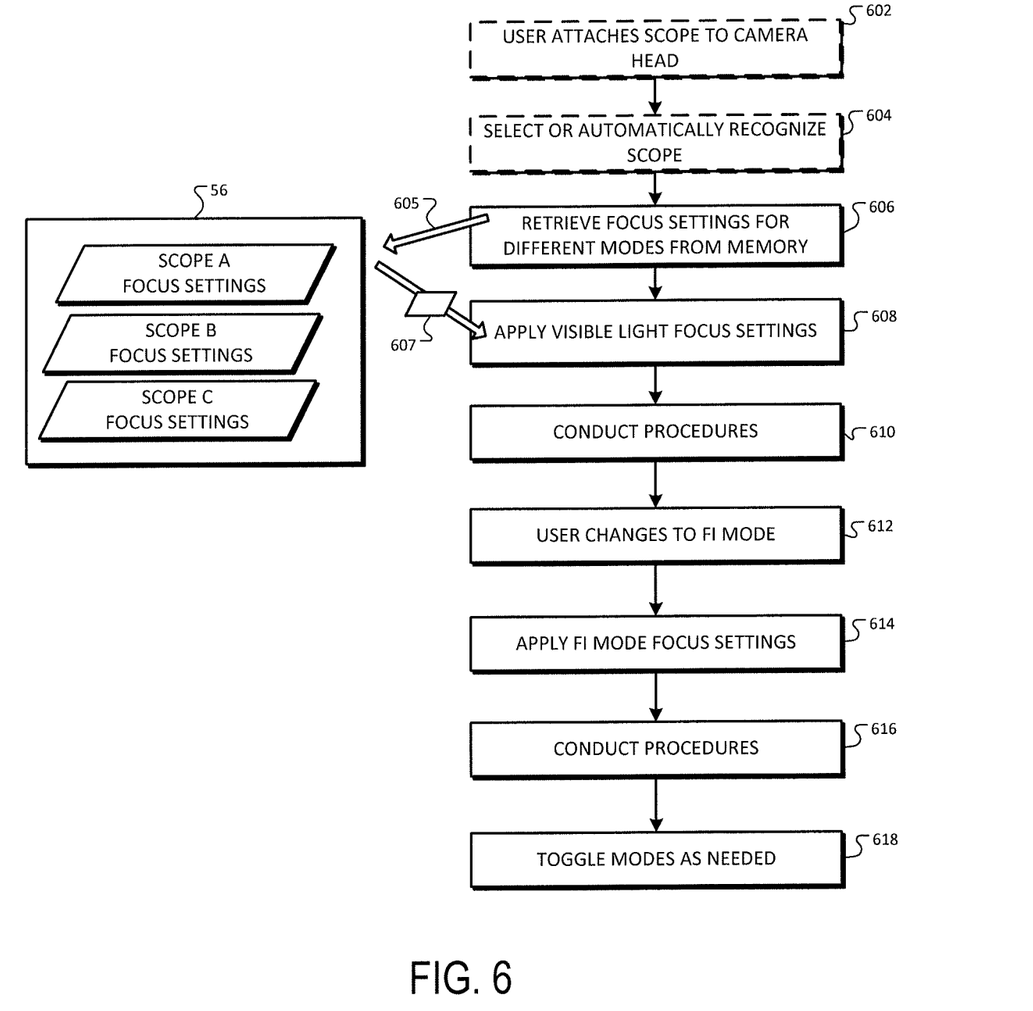
FIG. 6 is a flowchart of a process for applying device adjustments according to an example embodiment of the invention.

FIG. 6 is a flowchart of a process for controlling the automatic focus adjustment according to one embodiment of the present invention. The process may include attaching a new endoscope or other scope device to a first optical device such as a camera head at block 602, or powers on the first optical device which may have a new scope attached. Some versions may not include the steps of blocks 602 and 604. At block 604, the first optical device, alone or in cooperation with an attached CCM, recognizes the model of new scope has been attached, or the user selects through the CCM GUI the model of scope attached. The recognition may happen with any suitable means such as an RFID tag being recognized, or a serial number or other identifier being read from the second optical device, the scope, by the first optical device. Next at block 606, the process retrieves focus settings for the different available visible light and FI modes from memory as shown by arrows 605 and 607. The memory may hold focus settings for multiple scope models, including known, prescribed adjustments to provide the desired focal settings for each scope. The focus settings typically include control information for the automatic adjustment mechanism, such as actuator or piezo-electric motor positions for controlling the deformable lens or the sensor positioning mechanism as described above. For integrated scopes, such memory may be connected to a controller aboard the first optical device. For the preferred version in which a detachable camera head is used, the memory will typically be system memory 56 of the system CCM as shown, however onboard memory may be used in this case as well. The step of retrieving the settings may be performed by the CCM or the first optical device. Next at block 608, the first optical device applies the focus settings for the mode in which the first optical device is currently set, in this example the visible light mode is shown applied first. Then the first optical device may be used to conduct examination procedures as shown at block 610. Next at block 612, the user changes the mode to an alternate mode, in this case selecting the FI mode. This is typically done through a button or switch, or a foot pedal, on the first optical device but may be done through the CCM GUI. Then at block 614 the process applies the settings for FI mode, adjusting the sensor position or deformable lens as described above. This may involve another retrieval from memory or all mode settings may be held in working memory on the device or CCM. Then the device may be used to conduct examination procedures at block 616. The process may also include applying settings to change between different FI modes with different fluoresced light wavelengths. The FI mode may include simultaneous dual imaging with visible light images as discussed above. As shown at block 618, the modes may be toggled as needed with each change of mode applying the appropriate focus settings. As discussed above, the process may be conducted by program code running on system controller 50 on a system CCM, or may be conducted under control of program code or digital logic such as FPGA circuitry embodied in adjustment control circuitry 20 on the first optical device.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A camera head for use in endoscope procedures that attaches and detaches from an endoscope, and is operable to image in a first mode with white light at a first time interval and a second mode with fluoresced light outside the visible band at a subsequent, second time interval comprising:
    an image sensor assembly including a single and no more than one image sensor, the single image sensor operable for capturing both white light images and fluoresced light images; and
    a focus adjustment mechanism comprising a liquid-based, deformable lens, wherein the focus adjustment mechanism is positioned in the camera head and is configured to automatically adjust the focus of the camera head between two pre-determined states when the mode is switched from the white light mode to the fluoresced light mode, and wherein the automatic focus adjustment compensates for a chromatic focal difference between the white light image and the fluoresced light image caused by the dispersive or diffractive properties of optical materials or optical design employed in an assembly construction of the camera head or the endoscope connected to the camera head, or both,
    wherein the camera head is configured to automatically recognize the endoscope and determine a necessary adjustment of the focus adjustment mechanism when automatically adjusting the focus between the two pre-determined states, that is when the mode is switched between the white light mode and the fluoresced light mode, the necessary adjustment between the two states determined based on the known dispersive or diffractive properties of optical materials or optical design employed in the assembly construction of the endoscope, obviating, thereby, a need to apply an autofocus processing when toggling between the two modes.

2. A first optical device for use in endoscope procedures and operable to image in a first mode with white light at a first time interval and a second mode with fluoresced light outside the visible band at a subsequent, second time interval comprising:
    an image sensor assembly including a single and no more than one image sensor, the single image sensor operable for capturing both white light images and fluoresced light images; and
    a focus adjustment mechanism comprising a liquid-based, deformable lens, wherein the focus adjustment mechanism is positioned in the first optical device and is configured to automatically adjust the focus of the first optical device between two pre-determined states when the mode is switched from the white light mode to the fluoresced light mode, and wherein the automatic focus adjustment compensates for a chromatic focal difference between the white light image and the fluoresced light image caused by the dispersive or diffractive properties of optical materials or optical design employed in an assembly construction of the first optical device or an optional second optical device connected to the first optical device, or both, wherein the focus adjustment having been automatically adjusted by the focus adjustment mechanism is a known, prescribed adjustment based on the known dispersive or diffractive properties of optical materials or optical design employed in the assembly construction of the first optical device and/or the second optical device, obviating, thereby, a need to apply autofocus processing when toggling between the two modes.

3. The device according to claim 1, wherein the device is adapted to trigger the automatic focus adjustment when the device is toggled between the white light mode and the fluorescence mode between the first time interval and the second time interval.

4. A first optical device for use in endoscope procedures and operable to image in a first mode with white light at a first time interval and a second mode with fluoresced light outside the visible band at a second time interval and comprising:
    an image sensor assembly including a single and no more than one image sensor operable for capturing both white light images and fluoresced light images;
    an optical assembly positioned in the first optical device, or in a second optical device that attaches to the first optical device, the optical assembly including one or more optical lens elements, all either fixed in place or adjustable by manual movements, and configured when attached to direct light received from a subject scene toward the image sensor assembly; and
    a liquid-based deformable lens in the first optical device optically arranged to be between the optical assembly and the image sensor and operable to automatically adjust the focus of the first optical device wherein the automatic focus adjustment compensates for a chromatic focal difference between the white light image and the fluoresced light image caused by the dispersive or diffractive properties of optical materials or optical design employed in an assembly construction of the first optical device or the second optical device, or both, wherein the adjustment is a known, prescribed adjustment to the focus adjustment mechanism based on the known dispersive or diffractive properties of optical materials or optical design employed in the assembly construction of the first optical device and/or the second optical device, obviating, thereby, a need to apply autofocus processing when toggling between the two modes.

5. The device according to claim 4, wherein the first optical device is camera head that attaches to and detaches from the second optical device, and the second optical device is an endoscope.

6. The device according to claim 5, wherein the camera head is configured to automatically recognize the second optical device and determine a necessary adjustment of the focus adjustment mechanism when automatically adjusting the focus between the two pre-determined states, that is when the mode is switched between the white light mode and the fluoresced light mode, the necessary adjustment between the two states determined based on known dispersive or diffractive properties of optical materials or optical design employed in the assembly construction of the second optical device.

7. The device according to claim 4, wherein the device is adapted to toggle the liquid-based deformable lens between two pre-determined states when the mode is switched from the white light mode at the first time interval to the fluoresced light mode at the second time interval.

8. The device according to claim 1, wherein the endoscope further comprises an identifier, such as an RFID tag or serial number, and the camera head recognizes the endoscope by the identifier.

9. The device according to claim 6, wherein the endoscope further comprises an identifier, such as an RFID tag or serial number, and the camera head recognizes the endoscope by the identifier.

10. The device according to claim 2, wherein the device is adapted to trigger the automatic focus adjustment when the device is toggled between the white light mode and the fluorescence mode between the first time interval and the second time interval.

* * * * *